United States Patent [19]
Fleenor et al.

[11] 4,163,392
[45] Aug. 7, 1979

[54] SAMPLER PURGE SYSTEM

[75] Inventors: Richard P. Fleenor, Santa Cruz; M. Rinley Deeds, Felton, both of Calif.

[73] Assignee: Manning Environmental Corp., Santa Cruz, Calif.

[21] Appl. No.: 947,742

[22] Filed: Oct. 2, 1978

[51] Int. Cl.² ............................................. G01N 1/14
[52] U.S. Cl. ................................................. 73/421 B
[58] Field of Search ............. 73/421 R, 421 B, 423 A, 73/425.6

[56] References Cited
U.S. PATENT DOCUMENTS

| | | | |
|---|---|---|---|
| 3,252,330 | 5/1966 | Kling | 73/423 A |
| 3,508,442 | 4/1970 | Lightner et al. | 73/423 A |
| 3,645,142 | 2/1972 | Turpin | 73/425.6 |
| 3,901,087 | 8/1975 | Fabritus | 73/421 B |

Primary Examiner—S. Clement Swisher

[57] ABSTRACT

An intake channel pre-conditioner for a fluid sampler wherein prior to fluid sampling, fluid is drawn from a fluid body to be sampled by a pressure source communicating with the channel. The drawn fluid is passed along most of the length of the intake channel and then expelled by the pressure source.

7 Claims, 2 Drawing Figures

SAMPLER PURGE SYSTEM

BACKGROUND OF THE INVENTION a. Field of the Invention

The invention relates to fluid samplers and more particularly to a purge system for fluid samplers.

b. Prior Art

In the field of water pollution control there is a need to take samples of rivers, sewers, drains and the like. In industrial hygiene applications, there is a similar need to sample industrial plants' liquid effluents. Often this is accomplished by automatic samplers in which a sample chamber is filled with a desired sample volume which is then transferred into sample containers for use in a testing device; a complete apparatus including sample chamber, containers and testing device being described in U.S. Pat. No. 4,098,305, assigned to the assignee of the present invention. After the test procedure is complete the sample is wasted.

In automatic samplers a plurality of sample chambers is frequently used, with a sample being taken periodically, perhaps every hour or more, perhaps every six hours. During this period, the nature of the sample may change slightly. For example, even a few parts per million of certain substances or a change of a few parts per million between samples may be a cause for concern. This means that the sampling apparatus must be sensitive and also that contamination of samples must be avoided and that cross contamination between samples be avoided.

In a prior co-pending application, Ser. No. 918,470, assigned to the assignee of the present invention, the problem of cross-contamination between samples in re-used sample containers was discussed. However, in the present invention our concern was for the intake channel which feeds the sample containers. This channel is frequently made up of hose, tubing, pipes and reservoirs between an intake source and a sample container.

One problem is that a small amount of the previous sample remains in intake channels of the prior art. When a subsequent sample is drawn into the intake chamber, a slight amount of sample cross contamination occurs. Frequently this is due to small kinks in the channel, or gravitationally uneven locales where tiny puddles of sample material may form. In other instances, sample material such as suspended solid material may merely adhere to the walls of the intake channel until a subsequent sample causes this material to move along with the new sample flow, again causing some sample cross-contamination.

Another problem is the introduction of biological material into samples, particularly the growth of algae between sampling intervals. If sampling times are more than a few hours apart, measurable amounts of algae may grow in the intake channel where tiny puddles of prior sample material resides. This algae would be swept along with the next sample to be introduced causing a source of contamination. It may also be possible for other undesired organisms to enter the intake channel between samples, since this channel is usually left in the fluid body to be sampled and is usually open for entry of suspended solid matter during the time a sample is drawn.

An object of the invention was to devise a fluid sampler in which the problem of sample cross-contamination in the intake channel could be eliminated. Another object was to avoid sample contamination by algae, or the like, or even larger organisms invading the intake channel.

SUMMARY OF THE INVENTION

The above objects have been achieved in a fluid sampler in which the intake channel is preconditioned. Prior to introduction of a new sample, the intake channel is filled as though to draw a new sample, but then the drawn material is expelled. This in effect washes the intake channel with fluid similar to that to be drawn. The intake channel is, to a great extent, cleared of old material which formed tiny puddles in the intake channel and adhered to the walls thereof. The new material which forms the tiny puddles and adheres to the walls thereof is of little consequence because it resembles the new sample about to be drawn. Moreover, algae and any other organisms have been expelled.

One end of the fluid channel communicates with a fluid to be sampled, while the opposite end communicates with a sample chamber. A reversible pressure means, such as an air compressor or a fluid pump, communicates with the channel, for drawing fluid to a predetermined point, short of the sample chamber. The arrival of fluid at this point is detected by a sensor which signals a controller which causes a pressure reversal. Fluid is now expelled from the intake channel until the intake channel is clear. After the intake channel has been cleared, a new fluid sample is drawn into a sample chamber until a predetermined volume is collected. The new sample should be substantially free from contamination or cross-contamination from the intake channel.

DESCRIPTION OF THE PREFERRED EMBODIMENT

Figure 1:
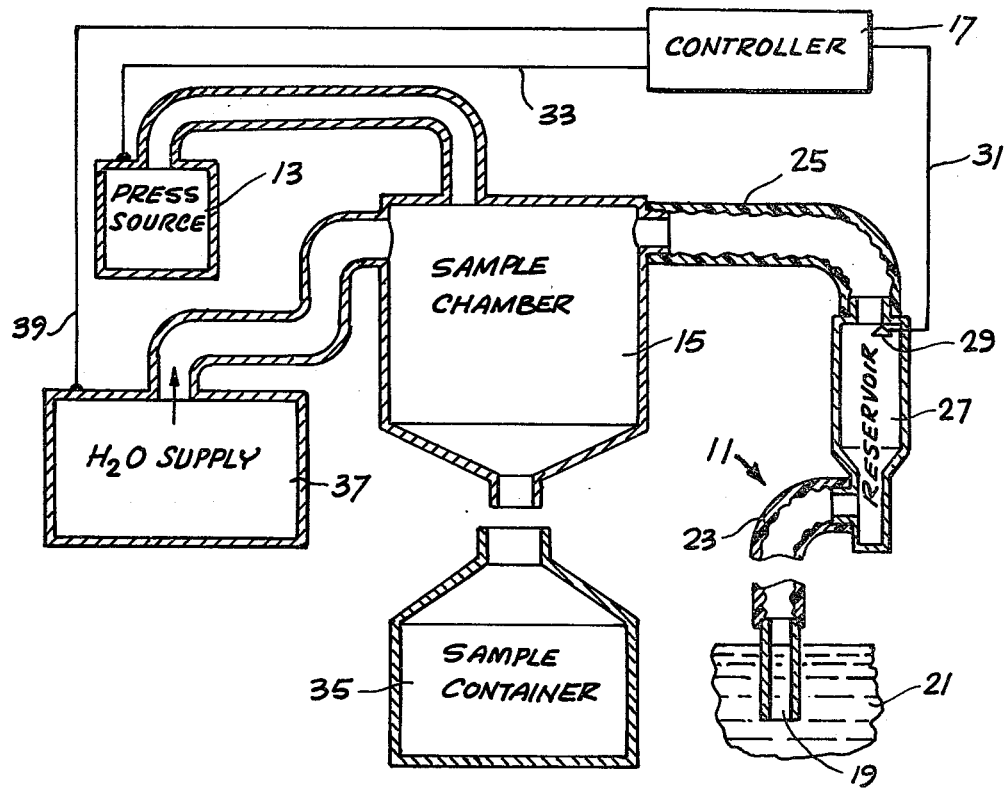
FIG. 1 is a plan view of the apparatus of the present invention.

The plan view of FIG. 1 shows an intake apparatus for a fluid sampler of the present invention. This apparatus, while not complete in all details, generally includes an intake channel 11, a pressure source 13 and a sample chamber 15. An electro-mechanical controller 17 has a timer for activating the pressure source 13 for drawing a sample by vacuum applied to the channel orifice 19 which is immersed in a fluid body 21 to be sampled.

The intake channel 11 may consist of a combination of hoses, pipes, tubes and passages which serve to conduct fluid from fluid body 21 to sample chamber 15. In FIG. 1, the intake channel is shown to consist of hose sections 23, 25 with a small fluid reservoir 27 interposed therebetween. The first hose section 23 is a relatively long section extending several feet, perhaps 10 or 12, from the sampler to a fluid body and is connected to the bottom of fluid reservoir 27, while the second hose section 25 is a relatively short section extending a few inches and connected to the top of the reservoir.

A sensor 29 is positioned near the top of reservoir 27 in the interior thereof so that fluid filling the reservoir will contact the sensor. The sensor 29 is a conductivity switch or differential pressure switch which will latch in a closed position when it is contacted by fluid filling reservoir 27. The switch is not affected by ambient dampness or droplets of fluid which may be sprayed onto it.

The closed switch generates an electrical signal transmitted to controller 17 over wire 31. Controller 17 may be an electro-mechanical device, including a clock and relays or preferably a completely electronic device. It is the function of the controller to regulate sampling intervals and to specify the sequence of apparatus operations. This is done by a semiconductor memory and associated logic circuits which execute the desired sequence on activation of an electronic clock or in response to manual instructions. The operation of the controller, as well as the entire apparatus will be described below.

Controller 17 is connected by wire 33 or by a pneumatic line to a reversible pressure source 13. This pressure source 13 is an air compressor having valves, either internal to the device or external, which communicates with hose section 25 through sample chamber 15. The valves can switch from positive to negative pressure, i.e., vacuum, on command of controller 17, signalling over wire 33.

Sample chamber 15 has a bottom valve, not shown, which is controlled by controller 17, and which permits transfer of sample material from sample chamber 15 to sample container 35. The purpose of sample chamber 15 is to receive a desired sample volume which is measured by a conductivity sensor, not shown, and transfer it to a sample container for further processing. Such further processing usually occurs at another location, with sample container 35 being replaced by another sample container.

Hose section 25 enters the top of sample chamber 15 at a tangential angle so that the fluid sample has rotational motion relative to the cone shaped interior of chamber 15. This vortex helps carry all sample materials, particularly suspended solids, which might otherwise adhere to the container walls. Vortex action is established when the valve at the bottom of chamber 15 is opened once a desired sample volume has been detected by the previously mentioned conductivity sensor. The sensor is mounted at a wall height in sample chamber 15 corresponding to the desired sample volume.

An optional fresh water supply 37 is connected to the top of sample chamber 15 for providing a source cleaning sample chamber 15 and for flushing hose sections 25, 23 and the interposed reservoir 27. The supply is operated by controller 37 which transmits electrical signals along line 39. A fresh water supply 37 is not usually provided for portable samplers which are frequently transported to remote sites. It is more common to find it used in fixed installations having ready access to fresh water. It is preferable that water from supply 327 enter the sample chamber 15 tangentially so that the water has rotational motion for forming a vortex once sample chamber 15 is opened.

In operation, controller 17 is programmed with the total time for taking samples and the number of samples to be taken. Immediately preceeding each sampling, one or more intake channel purge cycles is carried out.

A typical cycle is as pressure source 13 forces vacuum or negative pressure in chamber 15 which has a closed bottom valve. Vacuum is communicated into the intake channel 11 so that fluid enters hose section 23 and then reservoir 27. When fluid fills reservoir 27, sensor 29 is activated signalling controller 17 to reverse pressure from pressure source 13. Now positive air pressure fills sample chamber 15 and expels fluid from reservoir 27 and hose section 23.

After the desired number of intake channel purge cycles has been completed, an optional fresh water backwash cycle may be carried out if fresh water supply 37 is provided. Controller 17 opens a valve in the normally closed supply allowing fresh water under pressure to fill chamber 15 and overflow through intake channel 11 until water emerges through orifice 19. At that time the fresh water supply 37 is shut off and sample chamber 15 is then drained by dumping fresh water into a drain. Sample container 35 is moved out its receiving position for a sample in order that sample chamber 15 have access to a drain.

Figure 2:
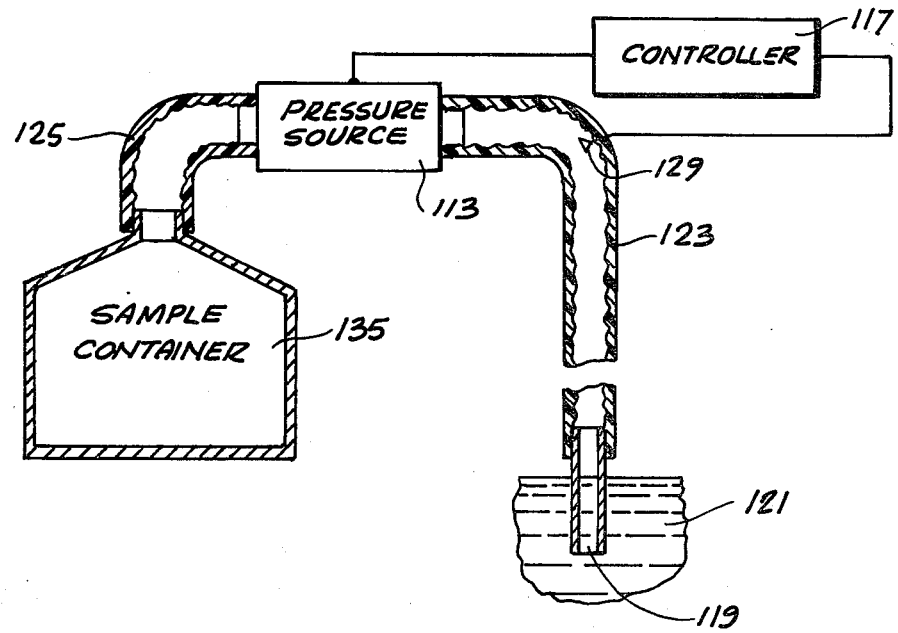
FIG. 2 is a plan view of an alternate embodiment of the apparatus of FIG. 1.

With reference to FIG. 2, an alternate intake preconditioner system is shown. The principal difference with respect to FIG. 1 is that the pressure source 113 is a fluid pump inserted between hose sections 123 and 125. Another difference is that a fluid reservoir has been omitted.

A fluid sensor 129 is positioned inside of hose section 123 near pressure source 113. When pressure source 113 pumps fluid from intake orifice 119 to the level of sensor 129, a signal is transmitted to controller 117 which reverses the pumping direction of pressure source 113. This cycle may be repeated a desired number of times.

Upon completion of the intake channel pre-conditioning cycles, as described above, pumping action is used to fill sample chamber 115 to the desired sample volume.

The apparatus shown in FIGS. 1 and 2 is usually enclosed in a weather tight enclosure as shown in U.S. Pat. No. 3,866,028, since samplers are frequently left out-of-doors. The apparatus in its portable form is powered by a battery pack, although regular a.c. may also be used and converted to d.c. for d.c. operation of sampler electrical systems.

We claim:

1. In a fluid sampler, an intake channel preconditioner system, comprising,
   an intake channel having a first end communicating with a fluid to be sampled and having a second end communicating with a sample container,
   reversible pressure means communicating with said channel for drawing said fluid up to a predetermined point in said channel and expelling fluid therefrom,
   control means connected to said reversible pressure means including a fluid sensor disposed at a predetermined point in said intake channel between said reversible pressure means and the first end of said intake channel and producing a signal on fluid contact, said control means for causing said reversible pressure means to draw and expel fluid in said channel.

2. The apparatus of claim 1 wherein said reversible pressure means is a compressor.

3. The apparatus of claim 1 wherein said reversible pressure means is a pump.

4. The apparatus of claim 1 wherein said intake channel comprises a hose.

5. The apparatus of claim 1 wherein said intake channel comprises a hose connected to a fluid reservoir having an inlet and outlet, said hose connected at said outlet, said predetermined point disposed proximate to the inlet thereof.

6. The apparatus of claim 1 wherein said intake channel preconditioner system further comprises a fresh water source communicating with said channel and with said control means whereby fresh water may be directed through said channel for washing.

7. The apparatus of claim 1 wherein said reversible pressure means is connected to the sample chamber which is connected by a hose to a fluid reservoir, which, in turn, communicates with a fluid to be sampled, said fluid reservoir having an inlet and outlet, said hose connected at said outlet, said predetermined point disposed proximate to the outlet thereof.

* * * * *